US006476239B1

(12) United States Patent
Arumugam et al.

(10) Patent No.: US 6,476,239 B1
(45) Date of Patent: Nov. 5, 2002

(54) PROCESS FOR THE PREPARATION OF ASCORBIC ACID

(75) Inventors: Bhaskar Krishna Arumugam, Kingsport, TN (US); Steven Thomas Perri, Kingsport, TN (US); Elaine Beatrice Mackenzie, Kingsport, TN (US); Larry Wayne Blair, Gate City, VA (US); Joseph Robert Zoeller, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/074,829

(22) Filed: Feb. 12, 2002

(51) Int. Cl.$^7$ ............................................ C07D 307/62
(52) U.S. Cl. ...................................................... 549/315
(58) Field of Search .......................................... 549/315

(56) References Cited

U.S. PATENT DOCUMENTS

| | | | |
|---|---|---|---|
| 2,185,383 A | | 1/1940 | Pasternack et al. |
| 2,462,251 A | | 2/1949 | Bassford, Jr. et al. |
| 2,491,065 A | | 12/1949 | Van Eekelen et al. |
| 2,956,070 A | | 10/1960 | Jennings et al. |
| 4,182,633 A | | 1/1980 | Ishikawa et al. |
| 4,764,276 A | | 8/1988 | Berry et al. |
| 4,923,616 A | | 5/1990 | Hirata et al. |
| 4,970,002 A | | 11/1990 | Ando et al. |
| 5,064,539 A | | 11/1991 | Tanimura et al. |
| 5,391,770 A | | 2/1995 | Le Far et al. |
| 5,405,992 A | * | 4/1995 | Funk et al. ............... 560/265 |
| 5,637,734 A | * | 6/1997 | Honda et al. ............. 549/315 |
| 5,744,618 A | | 4/1998 | Fechtel et al. |
| 5,744,634 A | | 4/1998 | Veits |
| 6,146,534 A | | 11/2000 | Grendze et al. |
| 6,153,791 A | | 11/2000 | Moore |

FOREIGN PATENT DOCUMENTS

| | | |
|---|---|---|
| DE | 199 38 980 A1 | 2/2001 |
| EP | 1 048 663 A1 | 11/2000 |
| JP | 48-15931 | 5/1973 |
| WO | WO 98/00839 | 1/1998 |
| WO | WO 99/03853 | 1/1999 |

OTHER PUBLICATIONS

U.S. patent application Ser. No. 09/975,872, Arumugan et al.
T. Reichstein, A. Grussner, *Helv. Chim. Acta* 17, p. 311–328, 1934.
Feng and Huang, Studies of a Membrane Reactor Esterification Facilitated by Pervaporation, Chemical Engineering Science, vol. 51, No. 20, pp 4673–4679, 1996.
Okamoto et al., Prevaporation–aided Esterification of Oleic Acid, Journal of Chemical Engineering of Japan, vol. 26, No. 5, pp. 475–481, 1993.
Kwon, et al Removal of Water Produced from Lipase–Catalyzed Esterification in Organic Solvent by Prevaporation, Biotechnology and Bioengineering, vol. 46, pp 393–395, 1995.
Keurentjes, The Esterification of Tartaric Acid with Ethanol: Kinetics and Shifting the Equilibrium by Means of Prevaporation, Chemical Engineering Science, vol. 49, No. 24A, pp. 4681–4689, 1994.
Xiuyuan, et al., Modified Aromatic Polyimide Membrane Preparation and Pervaporation Results for Esterification System, Water Treatment, 10, pp. 115–120, 1995.
Kawase et al., Increased Esterification Conversion by Application of the Simulated Moving–Bed Reactor, Chemical Engineering Science, vol. 51, No. 11, pp. 2971–2976, 1996.
Mazzotti et al., Dynamics of a Chromatographic Reactor: Esterification Catalyzed by Acidic Resins, Inc. Eng. Chem. Res. 1997, 36, 3163–3172.
Crawford et al. *Al. Adv. Carbohydrate Chemistry* 37, (1980), 79.
Ullman's Encyclopedia of Industrial Chemistry, vol. A27 (1996), 551–557.
D. B. Broughton, Production–Scale adsorptive separations of liquid mixtures by simulated moving bed technology, Separation Science and Technology, 19, 723 (1984–1985).
Wankat, Rate–Controlled Separations, Elsevier Applied Science, 1990, p. 524.
A. Navarro; H. Caruel; L. Rigal; P. Phemius, Continuous chromatographic separation process: simulated moving bed allowing simultaneous withdrawal of three fractions, Journal of Chromatography A, 770 pp. 39–50, (1997).
S. R. Perrin, R. M. Nicoud, Chiral Separation Techniques: A Practical Approach, Wiley VCH Verlag GmbH, Weinheim, 2001, Chapter 10, pp. 262–267.

* cited by examiner

*Primary Examiner*—Bernard Dentz
(74) *Attorney, Agent, or Firm*—Bernard J. Graves, Jr.; Cheryl J. Tubach

(57) ABSTRACT

The present invention is a process for the preparation of ascorbic acid using a simulated moving bed (SMB) reactor system to accomplish the simultaneous conversion of KLG or a derivative of KLG to ascorbic acid and the separation of reaction products. The SMB reactor contains a solid or mixture of solids effective for catalyzing the reaction of KLG or its derivative and for separating the reactions products by selective adsorption of at least one product. In a general embodiment, this process involves (1) feeding a solution of KLG or a derivative thereof in a first solvent and a desorbent which is miscible with the first solvent, to a simulated moving bed reactor; (2) reacting the KLG or the KLG derivative to form ascorbic acid; and (3) removing from the simulated moving bed reactor (i) a first liquid stream comprising a solution of ascorbic acid in the desorbent and the first solvent (ii) a second liquid stream comprising the first solvent and the desorbent.

19 Claims, 5 Drawing Sheets

US 6,476,239 B1

PROCESS FOR THE PREPARATION OF ASCORBIC ACID

FIELD OF THE INVENTION

This invention relates to a process for the preparation of ascorbic acid. More particularly, this invention pertains to a process wherein 2-keto-L-gulonic acid (KLG) or a KLG derivative is converted to ascorbic acid in simulated moving bed reactor (SMB).

BACKGROUND OF THE INVENTION

The commercial importance of ascorbic acid has resulted in numerous processes for its manufacture. Known commercial processes for the production of ascorbic acid generally involve four major steps: (1) a fermentation section where a sugar such as glucose or sorbose is subjected to fermentation to produce 2-keto-L-gulonic acid (KLG); (2) the purification and isolation of anhydrous KLG; (3) the conversion of the isolated KLG to an alkyl KLG ester (AKLG) by esterification with an alcohol, typically methanol; and (4) cyclization of the AKLG to produce L-ascorbic acid using stoichiometric amounts of a base. These processes have evolved from the original Reichstein Process (T. Reichstein, A. Grussner, *Helv. Chim. Acta* 17, p. 311, 1934).

The traditional Reichstein processes described above, in particular the last 3 steps, suffer from a number of disadvantages. For example, the esterification of KLG to an alkyl ester (Step 3) typically requires isolation of KLG as a solid from the aqueous fermentation broth by crystallization and drying. During crystallization of KLG, a significant amount of KLG present in the mother liquor stream may not be recovered. The isolated KLG normally must be free of water to obtain an acceptable yield of the ester of KLG in the subsequent esterification step. Drying KLG is normally accomplished by evaporation which requires large amounts of energy and costly equipment. This esterification is frequently carried out in anhydrous methanol using sulfuric acid or other strong acid catalysts which requires subsequent removal of the acid and its salts. For example, U.S. Pat. No. 5,391,770 describes a series of steps consisting of esterification of KLG with methanol in the presence of a strong soluble acid followed by a cyclization with an inorganic base and protonation with sulfuric acid. This is a lengthy process and requires crystalline KLG monohydrate and nearly anhydrous conditions to effect esterification and cyclization. U.S. Pat. No. 5,744,634 (European Patent Application EP 0 671 405 A) discloses a process for the production of the methyl or ethyl ester of KLG by esterification of KLG with methanol or ethanol in the presence of an ion exchange resin. The esterification process takes place in a tubular reactor containing an ion exchange resin using a residence time of from 10 to 120 minutes. The process disclosed in the '634 patent requires the monohydrate or, preferably, the anhydrous form to esterify KLG with methanol or ethanol.

The water formed during the esterification of KLG limits the equilibrium conversion and results in lost yield. As noted above, this problem is worsened if KLG monohydrate is utilized instead of anhydrous KLG and requires additional steps during the esterification to remove the water of hydration. An example of such a process is described in PCT Patent Application WO 99/03853.

Various processes to improve the esterification of KLG by increasing the efficiency of water removal have been described. U.S. Pat. Nos. 6,146,534 and 6,153,791 describe similar processes to dewater KLG solids using a solvent exchange process aided by ion exchange resins. Both processes accomplish separation only and an additional step to esterify KLG is required. The extent of esterification can be increased by simultaneously removing water or the ester as the reaction proceeds. WO 99/03853 discloses that the esterification of KLG may be carried out in a 2-stage process in which the reaction can be driven to completion by crystallization of methyl 2-keto-L-gulonate coupled with efficient removal of water. This process requires multiple crystallization stages and solid liquid separation equipment. German Patent Application DE 199 38 980 Al discloses a method for producing $C_1$–$C_{10}$ alkyl KLG esters by the esterification of KLG with a $C_1$–$C_{10}$ alcohol in the presence of an acid catalyst wherein the esterification is carried out in a liquid film on a hot surface with simultaneous removal of water. This process is simple to operate but requires significant energy and large volumes of alcohol solvent to act as a carrier for water removal. This process does not provide a means to remove impurities. Other known means to enhance the extent of esterification include membrane reactors for the selective removal of water during esterifications. These methods are well known and described in many publications, for example, by Feng. and Huang, Studies of a Membrane Reactor: Esterification Facilitated By Pervaporation, Chemical Engineering Science, Vol 51, No. 20, pp4673–4679, 1996; Jennings et al. U.S. Pat. No. 2,956,070; Okomoto et al., Pervaporation-aided Esterification of Oleic Acid, Journal of Chemical Engineering of Japan, Vol 26, No 5, pages 475–481, 1993; Kwon, et al, Removal of Water Produced from Lipase-Catalyzed Esterification in Organic Solvent by Pervaporation, Biotechnology and Bioengineering, Vol 46, pp 393–395, 1995; Keurentjes, The Esterification of Tartaric Acid with Ethanol: Kinetics and Shifting the Equilibrium by Means of Pervaporation, Chemical Engineering Science, Vol 49, No. 24A, pages 4681–4689, 1994; and Xiuyuam, et al., Modified Aromatic Polyimide Membrane Preparation and Pervaporation Results for Esterification System, Water Treatment, 10, pages 115–120, 1995. Simulated moving bed reactors have been proposed as another alternative to enhance the extent of esterifications. See, for example, Kawase et al., Increased Esterification Conversion By Application Of The Simulated Moving-Bed Reactor, Chemical Engineering Science, Vol 51, No 11, pages 2971–2976, 1996; Mazzotti et al., Dynamics Of A Chromatographic Reactor: Esterification Catalyzed By Acidic Resins, Ind. Eng. Chem. Res. 1997, 36,3163–3172; and U.S. Pat. No. 5,405,992. These publications describe processes that remove water formed during esterification of a carboxylic acid.

An improvement to the above processes is described by Arumugam et a/. in U.S. patent application Ser. No. 09/975, 872, filed Oct. 12, 2001. This process utilizes a SMB reactor to dewater, esterify KLG, and remove the water formed during esterification by the selective adsorption of water using an acidic ion-exchange resin. The process described in Arumugam et. al. does not, however, convert the KLG ester product into ascorbic acid.

Numerous processes for the preparation of ascorbic acid from KLG and esters of KLG have been published. Good reviews of the prior art are found in Crawford et. al. *Adv. Carbohydrate Chemistry*. 37, (1980), 79 and in *Ullman's Encyclopedia of Industrial Chemistry*, Vol. A27 (1996), 551–557. The conversion of KLG to L-ascorbic acid may be carried out by the original Reichstein process, or variants thereof, involving esterification with methanol followed by cyclization using stoichiometric amounts of a base. Alternatively, a diacetone-2-keto-L-gulonic acid intermediate may be cyclized directly, with loss of acetone followed by consecutive lactonization and enolization, to form ascorbic acid. Direct cyclization, however, requires extensive equipment for recovery of the acetone and other byproducts generated. Alternative methods involve the lactonization of KLG esters or KLG directly using acids. For example, U.S. Pat. No. 2,185,383 describes the reaction of KLG and its readily hydrolysable derivatives with concentrated hydrochloric acid in acetic acid solvent. A variant of this process is disclosed in U.S. Pat. No. 2,462,251 where 2-keto-L-gulonic acid is converted to ascorbic acid in an inert organic solvent under acidic conditions. Modifications to improve the process such as the use of surfactants (see e.g. U.S. Pat. No. 5,744,618; WO 98/00839; and JP-B 48-15931) or conducting the reaction in the melt phase (EP 1 048 663 A1) have been described. Generally, because of the decomposition of ascorbic acid in concentrated aqueous acids and its lack of solubility in inert organic solvents, these methods either do not provide satisfactory yields of ascorbic acid and or require lengthy purification procedures and extensive equipment to remove impurities that reduce product quality.

As is evident from the above discussion, the extant processes currently employed in the manufacture of ascorbic acid generally have a number of disadvantages, including: (1) high energy requirement and high capital and operating costs occasioned by the isolation of dry KLG; (2) yield loss during the purification of KLG; (3) incomplete conversion of KLG to its ester in the presence of water which is formed during esterification and/or present in the KLG as a result of the KLG manufacturing process; (4) removal of the homogenous acid esterification catalyst; (5) the, stoichiometric and, thus, costly use of $NaHCO_3$; and (6) the need for acidification of sodium ascorbate to produce ascorbic acid.

Thus, there exists a need in the art for an efficient and economical process for the preparation of ascorbic acid from KLG that avoids the disadvantages discussed above.

BRIEF SUMMARY OF THE INVENTION

The purpose of the present invention is to provide an efficient process for the preparation of ascorbic acid comprising the following steps:

I. feeding (i) a solution comprising 2-keto-L-gulonic acid (KLG) or a derivative thereof in a first solvent and (ii) a desorbent, which is miscible with the first solvent, to a simulated moving bed reactor containing a solid or mixture of solids effective for catalyzing reaction of KLG or the derivative thereof to ascorbic acid and for separating the reaction products by selective adsorption of at least one product;

II. reacting KLG or the derivative thereof to form ascorbic acid; and

III. removing from the simulated moving bed reactor (i) a first liquid stream comprising a solution of ascorbic acid in the desorbent and the first solvent and (ii) a second liquid stream comprising the first solvent and the desorbent.

An additional embodiment of the present invention is one where the aqueous solution of KLG is a product stream from a fermentation product for producing KLG. Another embodiment of this invention is one where a solution of an ester of KLG is fed to an SMB reactor containing a solid effective for catalyzing lactonization of the KLG ester. Yet another embodiment of the present invention is one which comprises the steps of:

I. feeding (i) an aqueous solution comprising KLG or a derivative thereof and (ii) a desorbent comprising an alcohol to a simulated moving bed reactor containing an acid ion-exchange resin effective for catalyzing esterification and lactonization of KLG or derivative thereof, and for separating the esterification or lactonization products by selective adsorption of at least one product;

II. reacting KLG or the derivative thereof and the alcohol to form an ester of KLG and ascorbic acid; and III. removing from the simulated moving bed reactor (i) a first liquid stream comprising a solution of ascorbic acid in the desorbent and (ii) a second liquid stream comprising water from the aqueous solution of Step (I), water formed during esterification of KLG and the alcohol, and the desorbent.

Figure 1:
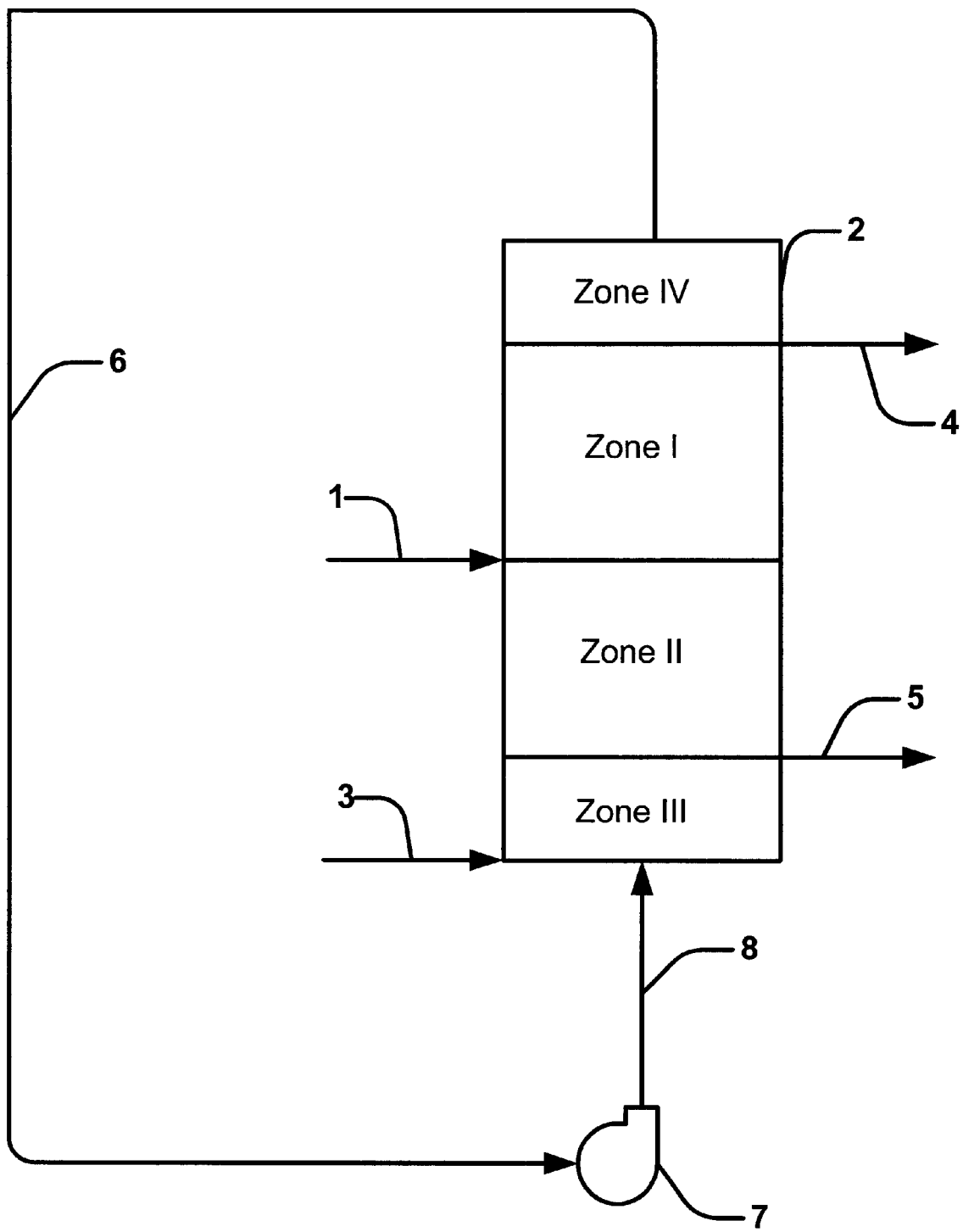
FIG. 1 is a schematic and process flow diagram illustrating a simple simulated moving bed reactor system for producing ascorbic acid according to the present invention utilizing 2 feed streams for the KLG and the desorbent, respectively, and 2 effluent streams from the reactor.

While the invention is susceptible to embodiment in various forms, there is shown in accompanying FIGS. 1, 2 and 3 and hereinafter described in detail a specific embodiment of the invention. The present disclosure is to be considered as an exemplification of the invention without limitation to the specific embodiment illustrated.

DETAILED DESCRIPTION

The present invention is a process for the preparation of ascorbic acid using a simulated moving bed (SMB) reactor system to accomplish the simultaneous conversion of KLG or a derivative of KLG to ascorbic acid and the separation of reaction products. The SMB reactor contains a solid or mixture of solids effective for catalyzing the reaction of KLG or its derivative and for separating the reactions products by selective adsorption of at least one product. In a general embodiment, this process involves (1) feeding (i) a solution comprising 2-keto-L-gulonic acid (KLG) or a derivative thereof in a first solvent, and (ii) a desorbent, which is miscible with the first solvent, to a simulated moving bed reactor containing a solid or mixture of solids effective for catalyzing reaction of KLG or a derivative thereof to ascorbic acid, and for separating the reaction products by selective adsorption of at least one product; (2) reacting KLG or the derivative thereof to form ascorbic acid; and (3) removing from the simulated moving bed reactor (i) a first liquid stream comprising a solution of ascorbic acid in the desorbent and the first solvent and (ii) a second liquid stream comprising the first solvent and the desorbent.

The simulated moving bed reactor utilized in the present invention is a known apparatus and comprises one or more chambers or columns, each of which contains a solid or mixture of solids. As depicted in FIG. 1, the SMB reactor (1) may consist of one or more sections comprising a plurality of zones shown in FIG. I as zone I, II, III and IV and, typically, is equipped with a plurality of inlet and outlet ports. In the present invention, the SMB reactor typically has 4–20 sections. The SMB reactor is packed with a solid or mixture of solids effective for catalyzing the reaction of KLG or a derivative of KLG to ascorbic acid and separating the reaction products by selective adsorption. For example, the reactor may be equipped with two inlet streams, the first a feed stream containing KLG dissolved in the first solvent and, the second, a feed stream for the desorbent or displacer. The reactor is equipped with a rotary valve or a plurality of valves arranged in a manner such that any feed stream may be introduced to any section or zone and any outlet or effluent stream may be withdrawn from any section or zone. During the operation of the SMB unit, the sections to which the feed streams are fed and from which the outlet streams are withdrawn are periodically moved. To achieve separation of reaction products, the locations of the inlet and outlet streams are moved intermittently in the direction of liquid flow. The intermittent port movement in the direction of liquid flow simulates the counter-current movement of the bed or beds of the solid(s), e.g., the solid catalyst. Different equipment and operational strategies have been used to simulate the counter-current movement of the solid with respect to the liquid. See, for example, D. B. Broughton, Production-Scale adsorptive separations of liquid mixtures by simulated moving bed technology, Separation Science and Technology, 19, 723 (1984–1985) and U.S. Pat. No's. 4,764,276, 4,923,616, 4,182,633, and 5,064,539. The process of the present invention may be carried out with all such variations of the SMB concept. A detailed description of the basic SMB process is provided by Wankat, Rate-Controlled Separations, Elsevier Applied Science, 1990, page 524 and a description of the SMB reactor concept is provided by Mazzotti et al (Marco Mazzotti, Bernardo Neri, Davino Gelosa, and Massimo Morbidelli, Dynamics Of A Chromatographic Reactor. Esterification Catalyzed By Acidic Resins, Ind. Eng. Chem. Res. 1997, 36,3163–3172).

The process provided by the present invention may be employed to produce ascorbic acid from KLG or derivative of KLG. The derivative of KLG may be any compound of KLG which is commonly available, e.g., a product from a fermentation process, or which is useful to improve the solubility of KLG or the conversion of KLG to ascorbic acid. Suitable derivatives of KLG include, but are not limited to, esters, acetals, ketals, or salts of KLG. The preferred forms of KLG are KLG, esters of KLG, or salts of KLG. The solid or mixture of solids used in the SMB are selected on the basis of the form of KLG used, e.g., acid or ester, the solvent used for KLG, the desorbent, and the desired separation. If KLG is used as the starting material, for example, a solid exhibiting acidic properties may be selected. If an ester of KLG is used, acidic or basic solids can be used to accomplish the conversion to ascorbic acid.

Although a salt of KLG may used as a feed material, it is preferred that the KLG present is in the form of the free acid, rather than as a salt. If large amounts of cations such as calcium ions are present, the effectiveness of the catalyst may be diminished. Thus, it is preferred that cations such as calcium, sodium, magnesium, and potassium ions are removed if they should be present in the aqueous KLG feed solution. Such cations may be removed according to conventional procedures such as, for example, precipitation using sulfuric acid and using strongly acidic cation exchange resins. Anions such as sulfates, phosphates, and chlorides may be removed from the aqueous feed although it is not necessary. The anions and cations also may be removed by alternate processes such as electrodialysis. If anions are not removed from the KLG feed solution, some of the anions may be removed in the SMB reactor along with water which is withdrawn as the second liquid stream. Alternatively, anions may be removed as a separate third stream using a modified SMB operation such as the procedures described in U.S. Pat. No. 4,970,002 and by A. Navarro; H. Caruel; L. Rigal; P. Phemius, Continuous chromatographic separation process: simulated moving bed allowing simultaneous withdrawal of three fractions, Journal of Chromatography A, 770 pages 39–50, (1997). FIG. 2 shows a schematic representation of one implementation of a SMB to withdraw three products. The operation is similar to the operation of a typical four zone SMB except that a third stream (Stream 9 in FIG. 2) is withdrawn from the SMB reactor. This third stream will contain impurities such as organic and inorganic acids, their esters, and other byproducts.

The KLG feed solution may comprise a single solvent or mixture of solvents. The solvent may be water, an alcohol, e.g., a straight- or branched-chain, unsubstituted or substituted alcohol containing up to about 8 carbon atoms. The process, however, may be employed advantageously even with anhydrous KLG, KLG monohydrate, a concentrated aqueous solution of KLG, or a solution of KLG in a solvent other than water since the process provides a means to remove the water released during any esterification and lactonization reactions. Diols such as ethylene glycol also may be used. Solvents other than alcohols such as nitriles, e.g., aceto-nitrile, ketones, and aliphatic and cyclic ethers, e.g., dim ethyl ether, tetrahydrofuran, and dioxane may be used. If necessary, the solvent properties of the KLG acid feed solution may be modified by using a co-solvent or mixture of solvents such as ethanol-cyclohexanone and tetrahydrofuran-methanol.

The process of our invention is particularly useful for the production of ascorbic acid using an aqueous fermentation broth containing KLG as a feed because of the dewatering capabilities of the SMB reactor. The fermentation broth typically is produced by the cultivation of one or more microorganisms to produce KLG and/or a derivative thereof. In addition to KLG and water, these fermentation broths typically contain other dissolved materials such as the nutrients required by the microorganism(s) being employed to produce KLG including, for example, amino acids, inorganic and/or organic salts, carbohydrates such as glucose, sorbose, mannose, disaccharides, and trisaccharides, depending upon the sugar feedstock to the fermenter, and various growth factors. The fermentation broth normally is filtered to remove biomass and other insoluble materials and may be treated with activated charcoal for color removal prior to being used in our novel reaction/solvent exchange/purification process.

The fermentation broth comprising an aqueous solution of KLG is fed to the simulated moving bed reactor in accordance with the present invention typically comprises about 0.5 to 50 weight percent, more typically about 7 to 15 weight percent, KLG; and about 50 to 98 weight percent, more typically about 75 to 95 weight percent, water. The weight ratio of dissolved KLG to dissolved impurities may be in the range of about 2:1 to 10:1.

The desorbent which is introduced to the SMB reactor contains a liquid capable of displacing a selectively adsorbed reaction product from the bed. The desorbent may be water, an alcohol, e.g., a straight- or branched-chain, unsubstituted or substituted alcohol containing up to about 8 carbon atoms that is miscible with KLG acid feed stream under the operating conditions. Diols such as ethylene glycol also may be used as the desorbent. If the desorbent is an alcohol, it may also serve as a reactant for the esterification of KLG in the presence of a suitable esterification catalyst within the SMB. Desorbents other than alcohols such as nitrites, e.g., aceto-nitrile, and aliphatic and cyclic ethers, e.g., dimethyl ether, tetrahydrofuran, and dioxane may be used. If necessary, miscibility of the desorbent and the KLG acid feed stream may be facilitated by varying the temperature and/or using a co-solvent or other additive which may be added to either the carboxylic acid feed stream or the desorbent. Solvent pairs such as ethanol-cyclohexanone and tetrahydrofuran-methanol are examples of the use of a co-solvent to make the desorbent miscible with the KLG feed solution. If the desorbent is a mixture of solvents, the desorbent mixture may be fed into the SMB reactor at single location or the individual solvent components of the desorbent may be fed at multiple locations.

In the present invention, the KLG feed solution and the desorbent are feed into the SMB reactor at at least 2 locations. If the desorbent is a mixture of solvents, then the KLG feed solution, the desorbent, or the individual components of the desorbent may be fed into the SMB at more than 2 locations, as discussed previously, for operational convenience or to facilitate the reactions and/or adsorption phenomena occurring within the SMB. Typically, the volume ratio of the amount of desorbent fed to the SMB reactor per volume of KLG feed solution is in the range of about 1:1 to 10:1 with a volume ratio of 2:1 to 4:1 being more preferred.

The simulated moving bed reactor contains a solid or mixture of solids effective for catalyzing the reaction of KLG or a derivative thereof to ascorbic acid and for separating the reaction products by selective adsorption of at least one product. The solid or mixture of solids is by necessity insoluble in the feed solution solvent, desorbent, any optional co-solvent, or other additive employed. Where one solid is used, the solid must effectively perform both the catalyst function and adsorption function. The choice of a suitable solid or mixture of solids is dependent on the nature of the KLG feed solution and the desorbent. For example, in one embodiment of the present invention where an aqueous solution of KLG and a desorbent are fed to an SMB reactor, an acidic. ion-exchange resin may be used to catalyze lactonization of KLG and for separating the reaction products of lactonization, water, and the desorbent. The term lactonization means the cyclization of KLG to form a cyclic ester or lactone, in this case ascorbic acid, through an internal esterification or trans-esterification reaction. If the aqueous feed solution contains an ester of KLG, acidic or basic ion-exchange resins are suitable catalysts for lactonization to ascorbic acid. In another embodiment of the present invention, KLG and an alcohol are fed to a SMB reactor containing an acidic ion-exchange resin suitable as a catalyst for esterification of KLG to an ester of KLG and for lactonization of the ester and any unreacted KLG to ascorbic acid. The alcohol, which serves as a reactant for esterification, can be introduced to the SMB reactor as a separate feed or as a cofeed with the KLG feed solution or with the desorbent. The simulated moving bed reactor optionally may be packed with more than one type of material. For example, it is possible to use a solid that is optimized for the conversion of KLG or a KLG derivative to ascorbic acid and another solid for adsorption and separation of reaction products and impurities. The simulated moving bed unit may be packed with a uniform mixture of two (or three) solid materials or the solid materials may be packed in different segments. Examples of suitable solid catalysts include zeolites, alumina, silica, silica-alumina, titania, acidic ion-exchange resins and basic ion-exchange resins. Examples of solids suitable as adsorbents include activated carbon, molecular sieves, alumina, silica, silica-alumina, titania, and non-acidic macroreticulated polymeric resins. It is understood that different KLG derivatives, solvents, and desorbents may require different ratios of catalyst to adsorbent and different catalyst to adsorbent combinations.

The effluent from the SMB reactor is removed in two or more liquid streams. Typically, there are two liquid streams: a first liquid stream comprising a solution of the ascorbic acid product in which the major solvent component is the desorbent and the minor component is the solvent from the KLG liquid feed and a second liquid stream containing reaction products, such as water and other impurities, in which the major solvent component is the solvent contained in the KLG feed and the desorbent as the minor solvent component. In one embodiment of the present invention where the KLG feed solution is the product of a fermentation process, the second liquid stream effluent also may comprise neutral or non-polar impurities, e.g., sugars, present in aqueous solution of KLG fed to the SMB reactor. Another embodiment of the present invention is to remove a third effluent stream from the SMB to take out additional organic and inorganic impurities.

The process of the present invention may be carried out over a broad range of temperature and pressure. The temperature may range from about 30° C. to 250° C. and is limited by the boiling point at the operating pressure of the materials fed to the SMB reactor. The preferred temperature range is about 70 to 150° C. More preferably, the operating temperature is between 90 and 120° C. Pressure is not a critical feature of the process. Thus, pressures between about ambient pressure and 3500 kPa gauge may be used. The preferred pressure range is between about 350 and 2000 kPa gauge.

In a preferred embodiment of the present invention, an aqueous solution of KLG or a derivative of KLG is fed to a section of the SMB unit. The KLG feed solution may contain additional impurities. A desorbent stream, which is either an alcohol, a solvent containing an alcohol, or mixture of solvents containing an alcohol, is fed to a different section of the SMB reactor containing an acidic ion-exchange resin effective for catalyzing esterification and lactonization of KLG or KLG derivative and for separating the esterification and lactonization products by the selective adsorption of at least one product. The alcohol functions, in combination with the solid packing, to separate the KLG or KLG derivative and water, to esterify KLG or KLG derivative to its ester, and to lactonize KLG and KLG ester that is formed to ascorbic acid. Two liquid effluent streams are removed from the SMB reactor: (i) a first liquid stream comprising a solution of ascorbic acid in the alcohol or a mixture of desorbent and the alcohol and (ii) a second liquid stream comprising water from the aqueous KLG feed solution, water from the esterification and lactonization reaction, impurities present in the KLG aqueous feed stream or formed as by-products of the esterification and lactonization reactions, the alcohol, and the desorbent.

The acidic catalyst present in the SMB reactor catalyzes the reaction of the alcohol with KLG to form an alkyl 2-keto-L-gulonate ester. Water formed during esterification is removed from the reaction region because of the resin's affinity for water. Thus, the reaction can be carried out substantially beyond the equilibrium conversion that would be achieved without the removal of water formed during esterification. Some or all of the KLG ester and unreacted KLG is converted by catalytic action of the acidic catalyst to ascorbic acid. The extent of conversion of the alkyl 2-keto-L-gulonate ester and KLG is dependent on the process temperatures. At temperatures below 30° C., the conversion of KLG or KLG ester to ascorbic acid is negligible. Beyond about 70° C., substantial amounts of KLG and KLG ester are converted to ascorbic acid. The preferred process temperature range is 90 to 120° C. and the preferred pressure range is between about 350 and 2000 kPa gauge.

The solid catalyst may be a zeolite or other inorganic, acidic material or, preferably, an acidic ion exchange resin, e.g., a macroreticulated polymeric material derived from styrene or styrene and divinylbenzene containing pendant sulfonic acid groups. Acidic ion exchange resins typically are capable of both catalyzing the conversion of KLG and KLG derivatives to ascorbic acid and separating water fed to and formed in the SMB reactor. Examples of such acidic ion exchange resins include Amberlyst® 15 marketed by Rohm and Haas Company, Dowex® Monosphere 99 H marketed by Dow Chemical Company, and Lewatit® M S100, SP112, K1221, and K2641 marketed by Bayer AG. Such acidic ion exchange resins have an affinity for water. The acid sites of the resin tend to exclude carboxylic acids such as KLG due to charge-charge repulsion. This mechanism is commonly referred to as "ion exclusion". The difference in the affinity of the acidic ion exchange resin for water and for a carboxylic acid such as KLG can be utilized advantageously to effect a separation between water present in the KLG feed and the carboxylic acid. Any neutral impurities present are not excluded by the acidic ion exchange resin since the neutral impurities are not charged molecules. A preferred embodiment of the process of the present invention takes advantage of the difference between the affinity of the acidic ion exchange resin catalyst for KLG and for neutral impurities (molecules which are not charged) to carryout the partial or complete separation of KLG from neutral impurities, e.g., uncharged sugars.

The alcohols which may be used in the process may contain up to about 8 carbon atoms and typically are unsubstituted or substituted aliphatic alcohols. Ethanol and methanol are the most preferred alcohol reactants.

The desorbent solvent preferably is an alcohol which functions as both the esterification reactant and desorber solvent. Most preferably, the desorbent is methanol or ethanol. However, an inert solvent (i.e., a non-reactive solvent) may be used as the desorbent, in which case the alcohol necessary to form the carboxylate ester may be introduced into the SMB reactor by mixing it with either the desorbent or the KLG feed or by feeding the alcohol separately. Examples of suitable solvents which may be used in addition to an alcohol as a desorbent include esters, diols, nitrites, ketones, and ethers. The volume ratio of the amount of desorbent, comprising the alcohol, a non-reactive solvent, or a mixture of a non-reactive solvent and an alcohol, i.e., feed components (ii) fed to the SMB reactor per volume feed component (i) (KLG or KLG derivative dissolved in a first solvent) fed normally is in the range of about 1:1 to 10:1 with a volume ratio of 2:1 to 4:1 being more preferred.

The effluent removed from the SMB reactor comprises a first liquid stream comprising a solution of ascorbic acid in the alcohol and any auxiliary solvents fed to the SMB as components of the desorbent and a second liquid stream comprising the solvent contained in the KLG feed, water of esterification, the alcohol, and the desorbent or desorbent components. In the preferred embodiment of the present invention, the second liquid stream effluent also may comprise neutral or non-polar impurities, e.g., sugars, present in aqueous. solution of KLG fed to the SMB reactor. In the preferred embodiment, the composition of the first liquid stream effluent typically comprises about 0.5 to 40 weight percent ascorbic acid, 0 to 25 weight percent KLG ester, 0 to 15 weight percent KLG, 0 to 25 weight percent water, about 50 to 95 weight percent of the alcohol, or mixture of alcohol and auxiliary solvent fed to the SMB reactor, and about 0 to 10 weight percent impurities which either originated from the fermentation broth/solution fed to the SMB reactor or formed as a byproduct of the esterification and lactonization reactions. For example, when using methanol as both the esterification reactant and desorbent, the first liquid stream effluent preferably comprises about 0.5 to 40 weight percent ascorbic acid, 0 to 25 weight percent methyl KLG, 0 to 25 weight percent KLG, 0 to 25 weight percent water, about 50 to 99 weight percent of methanol and about 0 to 10 weight percent impurities which originated from the fermentation broth/solution fed to the SMB reactor or formed as a byproduct of the esterification and lactonization reactions.

The second liquid effluent stream contains about 2 to 85 weight percent water, about 15 to 98 weight percent of the alcohol, or mixture of alcohol and auxiliary solvent fed to the SMB reactor, and about 0 to 30 weight percent impurities which either originated from the fermentation broth/solution fed to the SMB reactor or formed as a byproduct of the esterification or lactonization reactions. This stream may also contain some KLG, ascorbic acid, and KLG ester.

Another preferred embodiment is to remove a third liquid effluent stream from SMB reactor. This embodiment is particularly useful for the removal of additional organic and inorganic impurities. This stream typically comprises and aqueous solution of organic and inorganic impurities, the alcohol, and the desorbent if different from the alcohol Any KLG or KLG ester that was not converted to ascorbic acid in the first solution obtained from the simulated moving bed reactor may be cyclized directly without isolating the ester or KLG. For example, the KLG ester may be treated with an equivalent of an alkali metal bicarbonate, carbonate or alkoxide, e.g., sodium bicarbonate, sodium carbonate and sodium methoxide, to induce cyclization. The ascorbate product may then be isolated using conventional procedures. Alternatively, unconverted KLG or KLG ester present in the first solution obtained from the SMB reactor also may be cyclized to ascorbic acid in a solvent using an acid catalyst in a subsequent step (U.S. Pat. No's. 2,491,065 and 2,462, 251). The acid catalyst may be a homogenous acid such as sulfuric or hydrochloric acid or a solid acid catalyst.

It is also possible that any unreacted KLG and KLG ester can be separated from ascorbic acid and recycled back to the SMBR reactor along with the KLG feed. Alternatively, unreacted KLG or KLG ester may be separated from ascorbic acid and the ester converted to ascorbic acid by any of the methods described above. The separation of the KLG, KLG ester, and ascorbic acid may be accomplished by methods such as crystallization and chromatography.

The operation of the SMB reactor is described in detail herein for the formation of ascorbic acid via the esterification of KLG to methyl KLG followed by lactonization of methyl KLG and unreacted KLG to ascorbic acid. The SMB unit normally comprises a plurality of sections, typically 4–20 sections, packed with an acidic, cation exchange resin in hydrogen form.

Referring to accompanying FIG. 1, a fermentation broth comprising an aqueous solution containing approximately 10 weight percent KLG is fed via conduit 1 to SMB reactor 2 which typically is a cylindrical vessel filled with an acidic, ion exchange resin such as DOWEX Monosphere 99 H resin. SMB reactor 2 comprises 4 zones: I, II, III and IV as shown in FIG. 1. Methanol which functions as both desorbent and esterification reactant is fed to SMB reactor 2 through conduit 3. A portion of the contents of SMB reactor 2 is removed from the top of the SMB reactor and recycled via line 6, pump 7 and line 8 to the base of the SMB reactor. A first liquid product stream comprising ascorbic acid and unconverted methyl KLG and KLG in methanol, typically containing about 3 to 25 weight percent ascorbic acid and less than about 3% weight percent water, is removed from SMB reactor 2 via conduit 4. A second stream comprising water typically containing from 25 to 60 weight percent water and up to 5 weight percent impurities contained in the aqueous stream fed via conduit 1 is removed from the SMB reactor from conduit 5. The direction of liquid flow within SMB reactor 2 is set by the recycle pump and the direction of liquid flow is from Zone II to Zone I. The KLG-containing fermentation broth is fed between zones I and II of SMB reactor 2. KLG is excluded from the cation exchange resin by the ion exclusion mechanism. Water present in the feed stream is absorbed preferentially by the resin. The combination of ion exclusion of KLG and absorption of water by the acidic ion exchange resin, results in the resin possessing different affinities for KLG and water. As a result, KLG travels faster than water over and through the resin. By setting appropriate flow conditions in zones I and II and an appropriate step time for switching the locations of inlet and outlet streams, water can be separated from KLG and obtained as a separate stream which is withdrawn from a port located between zones II and III (conduit 5 in FIG. 1). As KLG separates from water, the methyl ester of KLG is formed by the catalytic action of the cation exchange resin. Methyl KLG and KLG is further converted to ascorbic acid by the catalytic action of the acid resin. Ascorbic acid is withdrawn from a port between zones I and IV (conduit 4 in FIG. 1).

Figure 2:
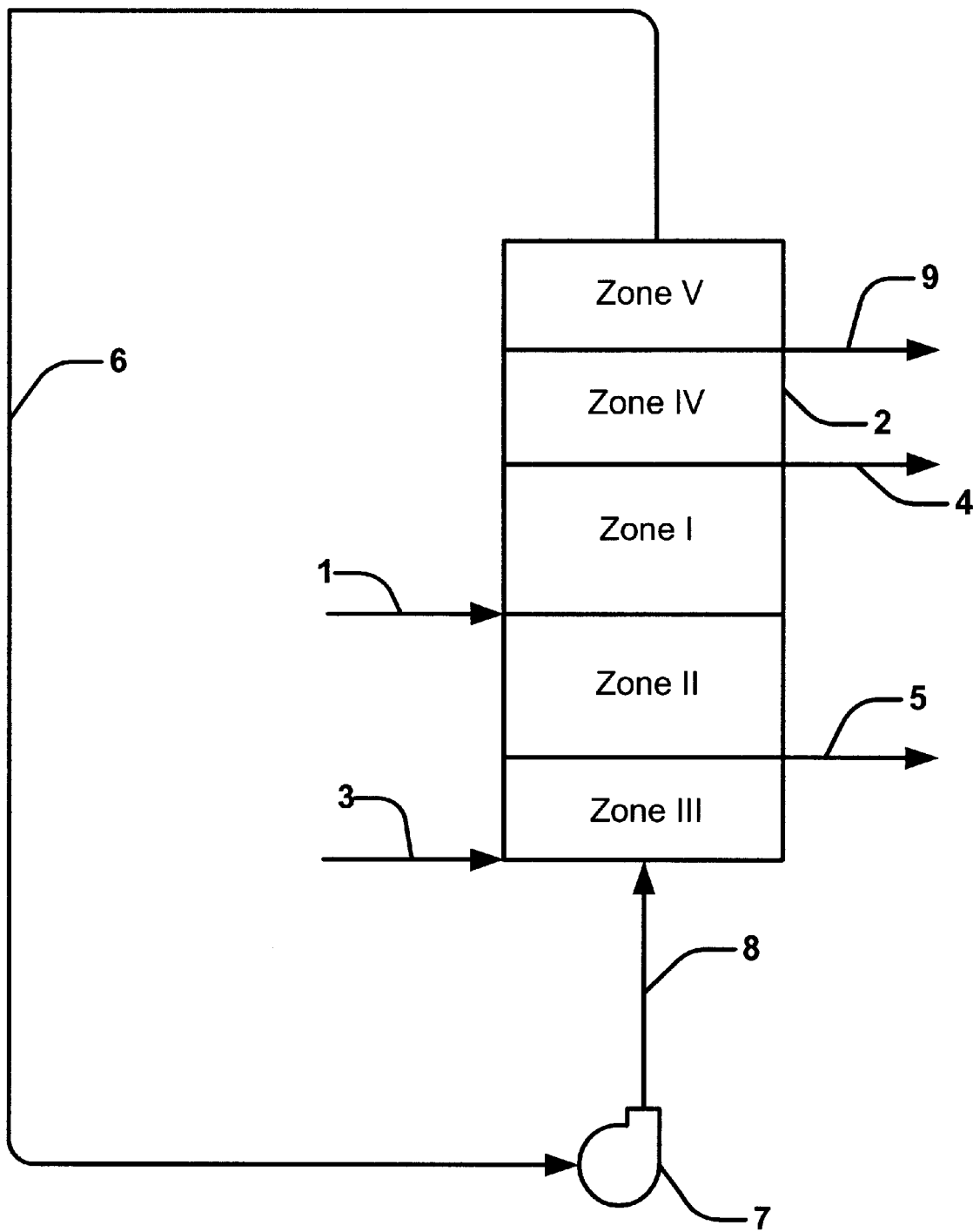
FIG. 2 is a schematic of the SMB reactor system utilizing 2 feed streams and 3 effluent streams from the reactor.
Figure 3:
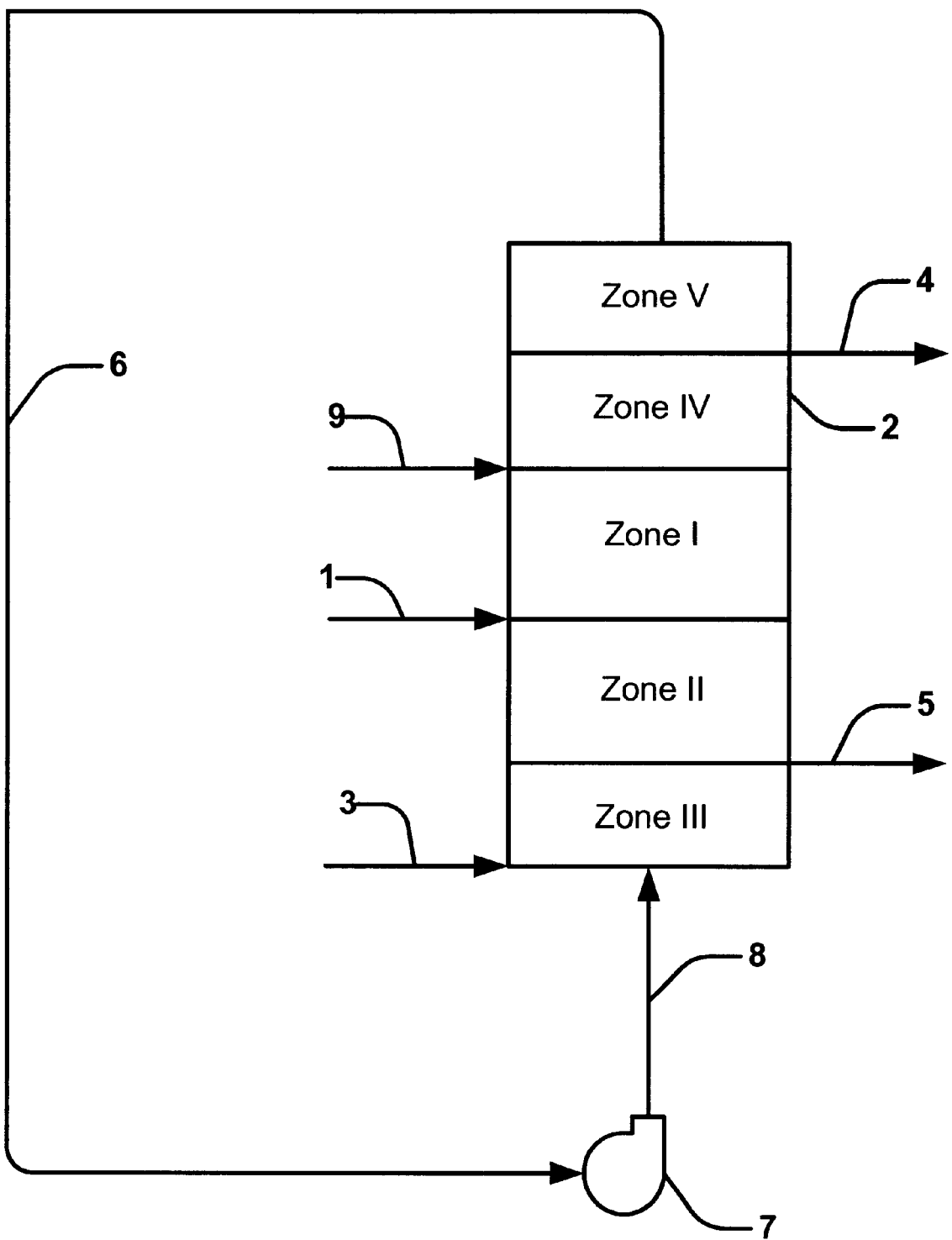
FIG. 3 is a schematic of the SMB reactor utilizing 3 feeds streams and 2 effluent streams from the reactor.

FIG. 2 is a process flow diagram similar to that described above for FIG. 1 comprising 5 zones: I, II, III, IV and V, which provides for the removal of inorganic acid and other impurities via a third effluent stream. The operation of SMB reactor 2 depicted in FIG. 2 is identical to the operation described above for FIG. 1 except that a third stream (conduit 9 in FIG. 2) is withdrawn from SMB reactor 2. This third stream typically contains impurities such as organic and inorganic acids thereof. Because these acidic impurities are stronger acids than KLG, they will be excluded from the acidic ion-exchange resin more than KLG and will travel faster through the column. FIG. 3 is a process flow diagram similar to that described above for FIG. 1 comprising 5 zones: I, II, III, IV and V, which provides for an additional feed of a desorbent. The operation of SMB reactor 2 depicted in FIG. 3 is identical to the operation described above for FIG. 1 except that a third inlet stream (conduit 9 in FIG. 3) is used to feed the alcohol required for esterification. If a solvent other than an alcohol is used as the desorbent, then the alcohol required for esterification may be introduced by premixing it with the feed stream, or by mixing it with the non-alcohol desorbent, or by feeding it as a separate stream as shown in FIG. 3.

EXAMPLES

The process provided by our invention is further illustrated by the following examples. All percentages given in the examples are by weight unless specified otherwise. KLG, KLG esters, and ascorbic acid were analyzed by liquid chromatography and water was analyzed by Karl-Fischer method. Pulse tests were conducted to determine the feasibility of an SMB separation. The use of laboratory pulse tests to determine the key operating parameters and as a test to establish the utility of an SMB for a specific separation is well known in the art (see, for example S. R. Perrin, R. M. Nicoud, Chiral Separation Techniques: A Practical Approach, Wiley-VCH Verlag GmbH, Weinheim, 2001, Chapter 10, pp. 262–267). A column is packed with a solid that is capable of separating the different components in the feed mixture. The column is preconditioned by pumping a mobile phase such as water or methanol. A pulse of the feed mixture is introduced into the column. This is followed by elution of the feed mixture by pumping the mobile phase through the column. Effluent fractions are analyzed and a chromatogram prepared by plotting the concentration of various components in the effluent fractions against the elution time or volume. A peak-to-peak separation between the elution peaks of the components to be separated demonstrates the feasibility of separation of the two components using a SMB or SMB reactor. A SMB or SMB reactor may be designed by those skilled in the art based on information obtained from pulse tests. In the examples presented here, pulse tests were carried using DOWEX Monosphere 99 H resin as the solid that separates KLG and water. The solid also serves as the acidic esterification and lactonization catalyst. Since the resin is supplied by the manufacturer in its calcium salt form, the resin was converted to its hydrogen form by passing 50 liters of 7% HCl solution over 10 liters of resin and subsequently rinsing the resin with 100 liters of water to remove HCl and calcium chloride. The DOWEX resin was presoaked in water and then packed in a metal column. The temperature in the column was maintained by circulating oil from an oil bath through the jacketed glass column. The DOWEX resin in the pulse test column was rinsed with methanol until the water level in the effluent from the column was below 1%. Pulse tests described in the examples were conducted either on the same column or on columns prepared in a similar fashion.

Example 1

A fermentation broth containing KLG as its calcium salt was acidified by adding concentrated sulfuric acid to precipitate calcium sulfate. The precipitated calcium sulfate was separated by filtration and the acidified broth was cation exchanged by passing it over Ambersep® 200H resin (Rohm and Haas Company) to reduce the level of cations. The cation-exchanged broth was anion exchanged by passing it over Duolite® A561 resin (Rohm and Haas Company) to remove anions such as sulfates, phosphates, and chlorides. The resulting solution comprised 9.26% KLG, 19 ppm Ca, 3 ppm Mg, 29 ppm K, 74 ppm Na, 51 ppm P, and 143 ppm S.

Figure 4:
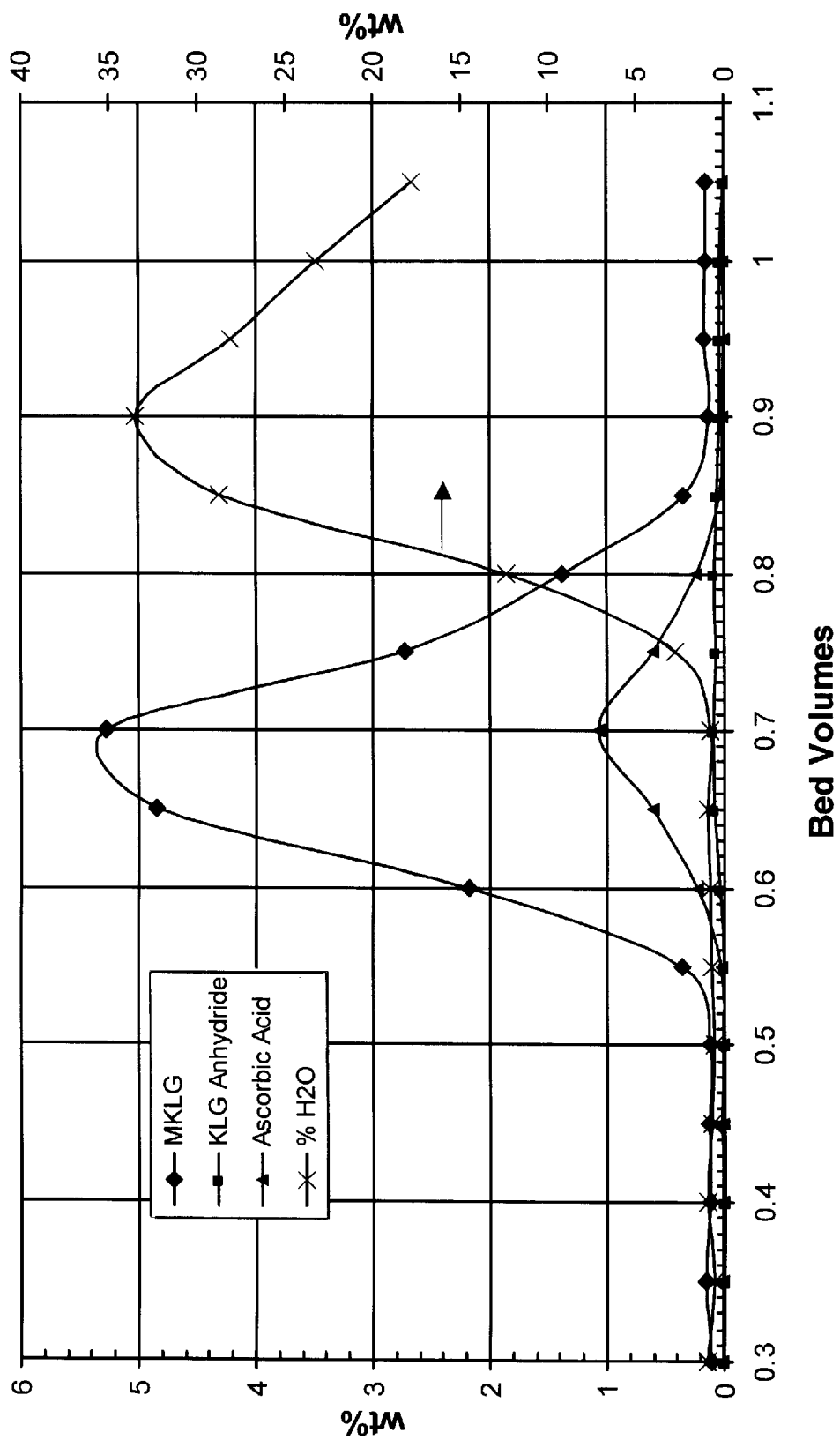
FIG. 4 is a graph showing the results of pulse tests as component concentration per bed volume for Example 1.

A pulse of 29.5 ml of the KLG solution prepared as described in the preceding paragraph was fed at a flow rate of 4.91 ml per minute to the pulse test column (volume=295 ml) described above and maintained at a temperature of 90° C. by circulating heated oil from an oil bath. The feed to the column was switched back to methanol after completion of the addition of the KLG solution. The effluent from the column was recovered in 14.75 ml fractions. These fractions were analyzed for KLG, ascorbic acid, MeKLG, and water. The results shown in FIG. 4 establish that KLG was converted to ascorbic acid though a significant amount of MeKLG remained unconverted. By raising the temperature and/or increasing the residence time, greater quantities of MeKLG may be converted to ascorbic acid. The results in FIG. 4 also established that there is a peak-to-peak separation between ascorbic acid and water. The horizontal axis is elution time, represented as bed volume. Bed Volume is calculated as:

$$\text{Bed Volumes} = \frac{\text{Volume of effluent collected}}{\text{Volume of column packing}}$$

Concentrations of eluting components is represented along the vertical axis. Since water is adsorbed by the resin, it elutes later than KLG which is excluded by the resin. The amount of KLG in the effluent fractions is negligible since KLG is converted to ascorbic acid and MeKLG by the catalytic action of the solid. Ascorbic acid elutes considerably earlier than water. There is a significant peak-to-peak separation between ascorbic acid and water and between KLG and water. A peak-to-peak separation between KLG and water in a pulse test demonstrates that KLG can be separated from water while simultaneously converting KLG to ascorbic acid.

Example 2

Figure 5:
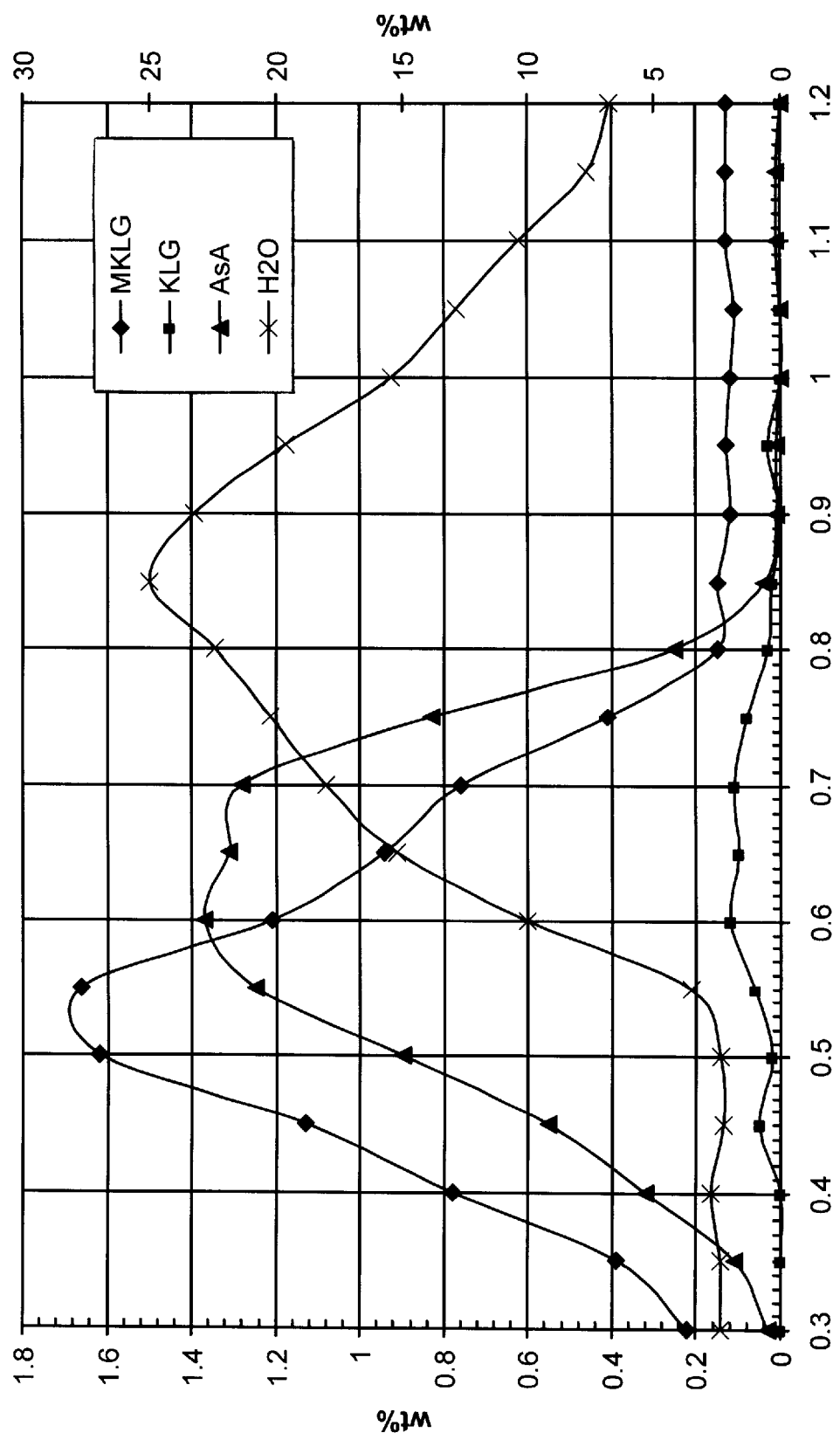
FIG. 5 is a graph showing the results of pulse tests as component concentration per bed volume for Example 2.

The feed prepared as described in Example 1 was used in this example. A pulse of 29.5 ml of the KLG solution prepared was fed at a flow rate of 4.91 ml per minute to the pulse test column (volume=295 ml) described above and maintained at a temperature of 110° C. by circulating heated oil from an oil bath. The feed to the column was switched back to methanol after completion of the addition of the KLG solution. The effluent from the column was recovered in 14.75 ml fractions. These fractions were analyzed for KLG, Ascorbic acid, MeKLG, and water. The results, shown in FIG. 5, establish that KLG was converted to ascorbic acid and that the amount of unconverted MeKLG was reduced significantly. There is a peak-to-peak separation between ascorbic acid and water indicating that it is feasible to operate a SMB reactor such that KLG fed to the reactor can be converted to ascorbic acid while simultaneously removing water present in the KLG feed and the water that is formed during the esterification of KLG.

The invention has been described in detail with particular reference to preferred embodiments thereof, but it will be understood that variations and modifications can be effected within the spirit and scope of the invention.

We claim:

1. A process for the preparation of ascorbic acid which comprises the steps of:
   I. feeding (i) a solution comprising 2-keto-L-gulonic acid (KLG) or a derivative thereof in a first solvent and (ii) a desorbent, which is miscible with the first solvent, to a simulated moving bed reactor containing a solid or mixture of solids effective for catalyzing reaction of KLG or the derivative thereof to ascorbic acid and for separating the reaction products by selective adsorption of at least one product;
   II. reacting KLG or the derivative thereof to form ascorbic acid; and
   III. removing from the simulated moving bed reactor (i) a first liquid stream comprising a solution of ascorbic acid in the desorbent and the first solvent and (ii) a second liquid stream comprising the first solvent and the desorbent.

2. Process according to claim 1 wherein the simulated moving bed reactor contains from 4 to 20 sections.

3. Process according to claim 1 wherein the derivative of KLG of Step I is an ester of 2-keto-L-gulonic acid.

4. Process according to claim 1 wherein the derivative of KLG of Step I is a salt of 2-keto-L-gulonic acid.

5. Process according to claim 1 wherein the first solvent is at least one solvent selected from the group consisting of water, alcohols, diols, esters, nitrites, ketones, and ethers.

6. Process according to claim 1 wherein the solution (i) of Step I is a product stream from a fermentation process for producing KLG or a derivative thereof.

7. Process according to claim 1 wherein the desorbent is at least one solvent selected from the group consisting of water, alcohols, diols, esters, nitrites, ketones, and ethers.

8. Process according to claim 1 wherein the Step I solution (i), the desorbent, or components of the desorbent are fed to the simulated moving bed reactor at at least 2 reactor locations.

9. Process according to claim 1 wherein the mixture of solids contains a solid effective for catalyzing the reaction of KLG or a derivative thereof to ascorbic acid selected from the group consisting of zeolites, alumina, silica, silica-alumina, titania, acidic ion-exchange resins and basic ion-exchange resins.

10. Process according to claim 1 wherein the mixture of solids contains a solid effective as an adsorbent selected from the group consisting of activated carbon, molecular sieves, alumina, silica, silica-alumina, titania, and non-acidic macroreticular polymeric resins.

11. Process according to claim 1 wherein the simulated moving bed reactor is maintained at a temperature of about 30 to 250° C. and a pressure of about 330 to 3500 kPa gauge.

12. Process according to claim 11 wherein the simulated moving bed reactor is maintained at a temperature of about 70 to 150° C.

13. A process for the preparation of ascorbic acid which comprises the steps of:
   I. feeding (i) an aqueous solution comprising KLG or a derivative thereof and (ii) a desorbent comprising an alcohol to a simulated moving bed reactor containing an acid ion-exchange resin effective for catalyzing esterification and lactonization of KLG or derivative thereof, and for separating the esterification and lactonization products by selective adsorption of at least one product;
   II. reacting KLG or the derivative thereof and the alcohol to form an ester of KLG and ascorbic acid; and
   III. removing from the simulated moving bed reactor (i) a first liquid stream comprising a solution of ascorbic acid in the desorbent and (ii) a second liquid stream comprising water from the aqueous solution of Step (I), water formed during esterification of KLG and the alcohol, and the desorbent.

14. Process according to claim 13 wherein the alcohol contains 1 to about 8 carbon atoms.

15. Process according to claim 13 wherein the desorbent comprises a mixture of the alcohol and at least one solvent selected from the group consisting of esters, diols, nitrites, ketones, and ethers.

16. Process according to claim 13 wherein the desorbent is methanol or ethanol and the simulated moving bed reactor is maintained at a temperature of 90 to 120 ° C. and a pressure of about 350 to 2000 kilopascals gauge.

17. Process according to claim 6 or 13 wherein the aqueous solution (i) of KLG or derivative thereof of step I comprises about 7 to 15 weight percent KLG and the first liquid stream (i) of step III comprises 0.5 to 40 weight percent solution of ascorbic acid in the alcohol.

18. Process according to 13 wherein the volume ratio of the aqueous solution of KLG or derivative thereof and desorbent of Step I is 1:1 to 1:10.

19. Process according to claim 13 wherein step III further comprises removing from the simulated moving bed reactor (iii) a third liquid stream comprising a solution of organic and inorganic impurities in the alcohol and the desorbent.

* * * * *

UNITED STATES PATENT AND TRADEMARK OFFICE
CERTIFICATE OF CORRECTION

PATENT NO.   : 6,476,239 B1
DATED        : November 5, 2002
INVENTOR(S)  : Arumugam et al.

It is certified that error appears in the above-identified patent and that said Letters Patent is hereby corrected as shown below:

Column 13,
Lines 29 and 35, "nitrites" should be -- nitriles --.

Column 14,
Line 29, "nitrites" should be -- nitriles --.

Signed and Sealed this

Eighteenth Day of February, 2003

JAMES E. ROGAN
*Director of the United States Patent and Trademark Office*